(12) United States Patent
Takahashi et al.

(10) Patent No.: US 9,833,447 B2
(45) Date of Patent: Dec. 5, 2017

(54) 5-HT4 RECEPTOR AGONIST FOR GASTROPARESIS

(71) Applicant: RAQUALIA PHARMA INC., Aichi (JP)

(72) Inventors: Nobuyuki Takahashi, Aichi (JP); Toshinori Yamamoto, Aichi (JP); Kaoru Shimada, Aichi (JP); Hirohide Noguchi, Aichi (JP)

(73) Assignee: RAQUALIA PHARMA INC., Aichi (JP)

( * ) Notice: Subject to any disclaimer, the term of this patent is extended or adjusted under 35 U.S.C. 154(b) by 0 days.

(21) Appl. No.: 15/306,914

(22) PCT Filed: May 18, 2015

(86) PCT No.: PCT/JP2015/002478
§ 371 (c)(1),
(2) Date: Oct. 26, 2016

(87) PCT Pub. No.: WO2015/174098
PCT Pub. Date: Nov. 19, 2015

(65) Prior Publication Data
US 2017/0056387 A1    Mar. 2, 2017

Related U.S. Application Data

(60) Provisional application No. 61/994,432, filed on May 16, 2014.

(51) Int. Cl.
*A61K 31/454* (2006.01)
*A61K 45/06* (2006.01)

(52) U.S. Cl.
CPC ............ *A61K 31/454* (2013.01); *A61K 45/06* (2013.01)

(58) Field of Classification Search
CPC .............................. A61K 31/454; A61K 45/06
See application file for complete search history.

(56) References Cited

U.S. PATENT DOCUMENTS

| 2003/0059374 | A1 | 3/2003 | Lehman et al. |
| 2005/0090554 | A1 | 4/2005 | Devane et al. |
| 2014/0051726 | A1* | 2/2014 | Takahashi ............ A61K 31/454 514/321 |

FOREIGN PATENT DOCUMENTS

| WO | WO 2006/090224 | * | 8/2006 | ........... C07D 413/12 |
| WO | WO-2006090224 A1 | | 8/2006 | |
| WO | WO-2012127878 A1 | | 9/2012 | |

OTHER PUBLICATIONS

International Search Report and Written Opinion for Application No. PCT/JP2015/002478, dated Aug. 18, 2015.
Eamonm MM Quigley, "Pharmacotherapy of gastroparesis", *Expert Opin. Pharmacotherapy*, vol. 1, No. 5, pp. 881-887, 2000.
Maeyer et al., "5-HT$_4$ receptor agonists: similar but not the same", *Neurogastroenterol Motil*, vol. 20, pp. 99-112, 2008.
Manabe et al., "New-generation 5-HT$_4$ receptor agonists: potential for treatment of gastrointestinal motility disorders", Expert Opin. Investig. Drugs, vol. 19, No. 6, pp. 765-775.
Soykan et al., "Demography, Clinical Characteristics, Psychological and Abuse Profiles, Treatment, and Long-Term Follow-up of Patients with Gastroparesis", *Dig. Dis. Sci.*, vol. 43, No. 11, 1998.
Hiba et al., "Is There a Difference in the Prevelance of Gastrointestinal Symptoms Between Type I and Type II Diabetics?", *Gastroenterology*, vol. 4, pp. A79, 1999.
McCallum et al., "Diabetic and Nondiabetic Gastroparesis", *Current Treatment Options Gastroenterology*, vol. 1, pp. 1-7, 1998.
Sturm et al., "Prokinetics in Patients with Gastroparesis: A Systematic Analysis", *Digestion*, vol. 60, pp. 422-427, 1999.
Jones et al., "Predictors of Delayed Gastric Emptying in Diabetes", *Diabetes Care*, vol. 24, No. 7, pp. 1264-1269, 2001.
Parkman et al., "Treatment of Patients with Diabetic Gastroparesis", *Gastroenterology & Hepatology*, vol. 6, pp. 1-16, 2010.

* cited by examiner

*Primary Examiner* — Erich A Leeser
(74) *Attorney, Agent, or Firm* — Marshall, Gerstein & Borun LLP

(57) ABSTRACT

This invention relates to 4-{[4-({([4-(2,2,2-trifluoroethoxy)-1,2-benzisoxazol-3-yl]-oxy}methyl)piperidin-1-yl] methyl}tetrahydro-2H-pyran-4-carboxylic acid for use in therapeutic treatment of the human body. In particular, it relates to the compound having selective 5-HT4 receptor agonism, which is useful for treating gastroparesis, or preventing or delaying the onset or the progression of gastroparesis.

6 Claims, 1 Drawing Sheet

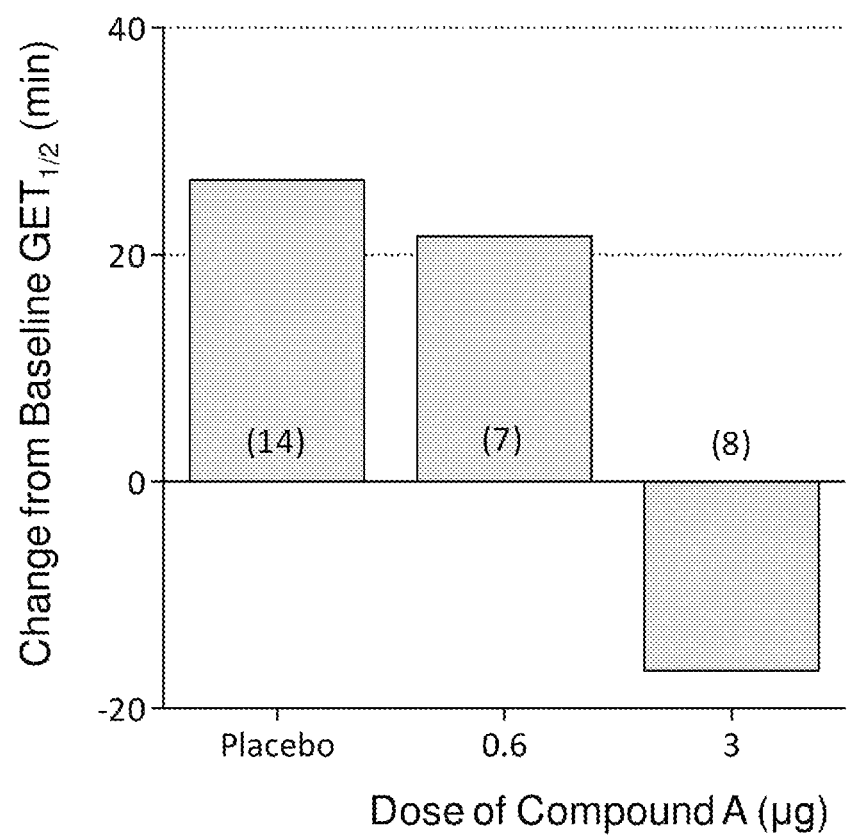
Values in the parenthesis indicates the number of subjects dosed.

5-HT4 RECEPTOR AGONIST FOR GASTROPARESIS

TECHNICAL FIELD

This invention relates to 4-{[4-({[4-(2,2,2-trifluoroethoxy)-1,2-benzisoxazol-3-yl]-oxy}methyl)piperidin-1-yl] methyl}tetrahydro-2H-pyran-4-carboxylic acid, which may be called Compound A through the present specification for use in therapeutic treatment of the human body. In particular, it relates to Compound A with selective 5-HT4 receptor agonism which is useful for treating gastroparesis, or preventing or delaying the onset or the progression of gastroparesis. This invention relates to a method for treating gastroparesis or a method for preventing or delaying the onset or the progression of gastroparesis, and these methods are characterized by causing fewer undesirable adverse events. In addition, this invention relates to a pharmaceutical composition for the treatment of gastroparesis or preventing or delaying the onset or the progression of gastroparesis, and this pharmaceutical composition is characterized by causing fewer undesirable adverse events. Furthermore, this invention relates to a compound for use in the treatment of gastroparesis or prevention or delay of the onset or the progression of gastroparesis, and this compound is characterized by causing fewer undesirable adverse events.

BACKGROUND ART

Gastroparesis, which means weak stomach, is a paralysis of the gastrointestinal (GI) system. It is a type of neuropathy causing stoppage or incorrect functioning of the autonomic nervous system resulting in delayed gastric emptying following ingestion of a meal. The stomach has two parts. The upper portion called the proximal stomach or fundus is where swallowed food and liquid collect. The lower portion called the distal stomach or antrum is where food is churned back and forth until it is broken into small fragments and then expelled into the duodenum which is the first part of the small intestine. Solid phase emptying is determined by powerful circular contractions of the antrum.

The vagus nerve controls the movement of food through the digestive tract. In normal individuals, a coordinated wave of activity sweeps across the antrum about three times a minute following ingestion of a solid meal causing the stomach to contract. Namely, the stomach empties within about 90-120 minutes after eating. When the vagus nerve is damaged or dysfunctional, stomach muscles do not work properly and stomach contraction becomes sluggish and/or less frequent. As a result, the movement of food is slowed or stopped. Gastroparesis is the medical term for this condition.

In individuals with gastroparesis, the electrical wave slows and the stomach contracts less frequently and sometimes with less force causing food to sit in the stomach. Normally, stomach muscles contract about three times a minute and the stomach empties within about 90-120 minutes after eating.

Major causes of gastroparesis include, but are not limited to, postviral syndromes, anorexia nervosa, surgery on the stomach or vagus nerve, medications, particularly anticholinergics and narcotics (or any other drugs that slow contractions in the intestine), gastroesophageal reflux diseases, smooth muscle disorders such as amyloidosis and scleroderma, nervous system diseases such as abdominal migraine and Parkinson's disease, and metabolic disorders such as hypothyroidism, multiple sclerosis, and drugs including anticholinergics, calcium channel blockers, opioids, antidepressants.

In 40% of the cases, gastroparesis has no known cause. The disease, however, occurs in approximately 25% to 35% of diabetics with one study finding the prevalence of the disorder to be as high as 59%. [{NPL 1} Soykan, I. et al., Demography, clinical characteristics, psychological and abuse profiles treatment and long-term follow-up of patients with gastroparesis, Dig. Dis. Sci. 11: 2398-2404, 1998; {NPL 2} Hiba, R., Is there a difference in the prevalence of gastrointestinal symptoms between type 1 and type 2 diabetics? Gastroenterology, 4: A79, 1999]. Therefore diabetes is also a major cause of gastroparesis. Blood glucose levels of diabetic patients often remain high for long periods. High blood glucose causes chemical changes in nerves and damages the blood vessels that carry oxygen and nutrients to the vagus nerve. As a result, at least 20% of people with Type I diabetes develop gastroparesis. Gastroparesis also occurs in people with Type II diabetes, although less often. It is not clear why the prevalence of this disease is so high in the diabetic population; however, it appears that glucose control is important since hyperglycemia causes delay in gastric emptying and exacerbates the symptoms associated with the disease.

Typical symptoms of gastroparesis include early satiety, weight loss, abdominal bloating, abdominal discomfort, epigastric pain, anorexia, nausea, and vomiting. These symptoms may be mild or severe. In addition, because food lingers in the stomach, gastroparesis can lead to complications such as bacterial overgrowth from fermentation of food, hardening of food into solid masses called bezoars that may cause nausea, vomiting, and obstruction in the stomach. Bezoars can be dangerous if they block the passage of food into the small intestine.

Treatments currently available are not fully efficacious and are often associated with undesirable adverse events. For example, prokinetic and antiemetic agents may be administered to treat delayed gastric emptying ({NPL 3} McCallum, R. et al. Diabetic and nondiabetic gastroparesis: Current Treatment Options Gastroenterology, 1: 1-7, 1998). The weak correlation between gastric emptying and the severity of symptoms is known ({NPL 4} Digestion, 60: 422-427, 1999; {NPL 5} Diabetes Care, 24: 1264-1269, 2001). Promotion of gastric emptying does not simply lead to the treatment of gastroparesis, which makes the treatment of gastroparesis difficult. The effective drug with enough safety is limited ({NPL 6} Gastroenterol Hepatol, 6: 1-16, 2010).

Intravenous erythromycin is often the treatment of choice for patients who cannot take oral medications due to the severity of the disease or other problems. However, erythromycin can cause GI toxicity, ototoxicity, pseudomembranous colitis, and the induction of resistant bacterial strains. Erythromycin is recognized that the effect is reduced by long-term use. No symptom improvement effect in patients with gastroparesis is observed in motilide, motilin-like macrolide. At a dose of promoting gastric emptying, motilin agonists (e.g. Erythromycin) cause accommodation inhibition, and worse early satiety of patients with gastroparesis.

For patients that can take oral medications, cisapride, which is 5-HT4 agonist, is probably the most efficacious. Cisapride has been withdrawn for safety reasons. Adverse events of cisapride include abdominal discomfort and increased frequency of bowel movements. In addition, there are important drug interactions that may cause heart arrhythmias; therefore, the drug is severely restricted as to its availability in the world. 5-HT4 agonists seem to be no problem from the mechanistic aspect in symptom improvement, because cisapride was applied to gastroparesis. But no 5-HT4 agonists have been clinically available yet.

Metoclopramide in oral and injectable forms is the only currently approved treatment for gastroparesis in the United States. Metoclopramide is a dopamine antagonist and acts by stimulating stomach muscle contractions to help empty food. Traditionally, treatment of gastroparesis with Metoclopramide is via injection or oral route.

Metoclopramide is currently available in tablet form, injection form, and syrup form, under the name REGLAN (A.H. Robbins Company). Tachyphylaxis may develop to the beneficial effects of Metoclopramide in some patients.

However Metoclopramide has a significant profile of adverse events that include fatigue, sleepiness, depression, anxiety, and difficulty with physical movement. Mental depression has occurred in patients with and without prior history of depression.

Symptoms range from mild to severe, including suicidal ideation and suicide. Other adverse events include involuntary movements of limbs and facial grimacing, torticollis, oculogyric crisis, rhythmic protrusion of tongue, bulbar type of speech, trismus, and dystonic reactions such as strider and dyspnea.

Further, domperidone is a less potent version of metoclopramide. In addition, anti-emetics are sometimes used to relieve one or more symptoms of gastroparesis (i.e., nausea, vomiting), but, unlike, for example, metoclopramide do not treat the underlying disorder by increasing gastric motility. In fact, gastroparesis involves multiple symptoms in addition to emesis, and the skilled practitioner would not expect a drug that treats emesis alone to be an adequate treatment of gastroparesis. Domperidone is not available in the United States for QT prolongation.

In patients with gastroparesis, absorption through the GI tract is unpredictable and far less effective the normal, with predictability and effectiveness having an inverse relationship to the severity of the symptoms.

Thus, the more severe the symptoms, the less likely that oral administration becomes an option for the treatment. Further complicating matter of oral administration is the fact that patients with gastroparesis often have symptoms such as vomiting and nausea. If vomiting takes place, the amount of oral dosage that remains in the stomach is unknown, and the result of treatment is even less predictable.

CITATION LIST

Patent Literature

{PL 1} WO2006/090224

Non Patent Literature

{NPL 1} Soykan, I. et al., Dig. Dis. Sci., 11: 2398-2404, 1998
{NPL 2} Hiba, R., Gastroenterology, 4: A79, 1999
{NPL 3} McCallum, R. et al., Current Treatment Options Gastroenterology, 1: 1-7, 1998
{NPL 4} Sturm, A. et al., Digestion, 60: 422-427, 1999
{NPL 5} Jones, K. et al., Diabetes Care, 24: 1264-1269, 2001
{NPL 6} Parkman, H. et al., Gastroenterol Hepatol, 6: 1-16, 2010

SUMMARY OF INVENTION

Technical Problem

In view of the above, there is clearly an unmet medical need regarding the treatment of gastroparesis. Potent drugs with improved safety for the treatment of gastroparesis have been awaited. Then, there is a clear need for improved methods of treating gastroparesis.

Solution to Problem

The present inventors made extensive research on medicinal agents for treating gastroparesis and found that Compound A having selective 5-HT4 receptor agonism exerts therapeutic effects for gastroparesis with fewer undesirable adverse events observed in conventional medications.

Thus, an object of the present invention is to provide Compound A having selective 5-HT4 receptor agonism, which is useful for treating gastroparesis, or preventing or delaying the onset or the progression of gastroparesis.

In addition, an object of the present invention is to provide a pharmaceutical composition for the treatment of gastroparesis, which comprises a therapeutically effective amount of Compound A or a pharmaceutically acceptable salt thereof, a method for the treatment of gastroparesis in an animal subject including a mammalian subject, which comprises administering to the animal subject including a mammalian subject Compound A or a pharmaceutically acceptable salt thereof, and a method for the treatment of gastroparesis in an animal subject including a mammalian subject, which comprises administering to the animal subject including a mammalian subject in need a therapeutically effective amount of Compound A or a pharmaceutically acceptable salt thereof.

The gastroparesis can be caused by conditions including diabetes, postviral syndromes, anorexia nervosa, surgery of the stomach or vagus nerve, amyloidosis, scleroderma, abdominal migraine, Parkinson's disease, hypothyroidism, multiple sclerosis, and drugs including anticholinergics, calcium channel blockers, opioids, and antidepressants. In addition, the gastroparesis can be a symptom of any of the foregoing conditions. The gastroparesis can be treated, while minimizing at least one undesirable adverse event associated with the administration of a conventional formulation of Compound A (4-{[4-({([4-(2,2,2-trifluoroethoxy)-1,2-benzisoxazol-3-yl]oxy}methyl)piperidin-1-yl]methyl}tetrahydro-2H-pyran-4-carboxylic acid) or a pharmaceutically acceptable salt thereof.

The gist of the present invention is as follows:

[1] a use of 4-{([4-({([4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof in the manufacture of a medicament for the treatment of gastroparesis in an animal subject including a mammalian subject;

[2] the use of item [1], wherein 4-{[4-({([4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof is used in combination with one or more additional compounds known to be useful in the treatment or prevention of gastroparesis or the symptoms thereof;

[3] a pharmaceutical composition for the treatment of gastroparesis, which comprises a therapeutically effective amount of 4-{([4-({([4-(2,2,2-trifluoroethoxy)-1,2-benzisoxazol-3-yl]oxy}methyl)piperidin-1-yl]

methyl}tetrahydro-2H-pyran-4-carboxylic acid or a pharmaceutically acceptable salt thereof;

[4] the pharmaceutical composition of item [3], which further comprises a therapeutically effective amount of one or more additional compounds known to be useful in the treatment or prevention of gastroparesis or the symptoms thereof;

[5] a method for the treatment of gastroparesis in an animal subject including a mammalian subject in need of such treatment, which comprises administering to the said subject an effective amount of 4-{([4-({[4-(2,2,2-trifluoroethoxy)-1,2-benzisoxazol-3-yl]-oxy}methyl)piperidin-1-yl]methyl}tetrahydro-2H-pyran-4-carboxylic acid or a pharmaceutically acceptable salt thereof;

[6] the method for the treatment of gastroparesis described in item [5], wherein at least one symptom of gastroparesis is relieved;

[7] the method according to item [6], wherein said gastroparesis is caused by at least one condition selected from the group consisting of diabetes, postviral syndromes, anorexia nervosa, surgery of the stomach or vagus nerve, amyloidosis, scleroderma, abdominal migraine, Parkinson's disease, hypothyroidism, multiple sclerosis, and drugs including anticholinergics, calcium channel blockers, opioids, antidepressants, or said gastroparesis is a symptom of any of the foregoing conditions;

[8] the method of item [5] to item [7], which comprises further administering a therapeutically effective amount of one or more additional compounds known to be useful in the treatment or prevention of gastroparesis;

[9] a method for the treatment of gastroparesis, which comprises administering a therapeutically effective amount of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof to an animal subject including a mammalian subject in need;

[10] the method of item [9], which comprises further administering a therapeutically effective amount of one or more additional compounds known to be useful in the treatment or prevention of gastroparesis;

[11] 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof for use in the treatment of gastroparesis in an animal subject including a mammalian subject;

[12] the compound or a pharmaceutically acceptable salt thereof according to item [11] for use in the treatment of gastroparesis, wherein said gastroparesis is lessened at least one symptom of gastroparesis; and

[13] the compound or a pharmaceutically acceptable salt thereof according to item [12], wherein said gastroparesis is caused by at least one condition selected from the group consisting of diabetes, postviral syndromes, anorexia nervosa, surgery of the stomach or vagus nerve, amyloidosis, scleroderma, abdominal migraine, Parkinson's disease, hypothyroidism, multiple sclerosis, and drugs including anticholinergics, calcium channel blockers, opioids, antidepressants, or said gastroparesis is a symptom of any of the foregoing conditions.

Advantageous Effects of Invention

It has now surprisingly been found that Compound A of this invention which has strong effects on gastric emptying is useful for the treatment of gastroparesis.

Namely, the present inventors discovered that Compound A of this invention has the desirable property for the treatment of gastroparesis using the clonidine-induced gastroparesis model in dogs. Compound A of this invention has also been discovered to have the much stronger (more than 3,000 times) potency than that of cisapride in the models above.

Further, the excellent effect of Compound A against gastroparesis has also been observed in human. Namely, the parameters for gastric emptying (GE), gastric half emptying time ($GET_{1/2}$) has been also improved following oral administration of Compound A to human.

BRIEF DESCRIPTION OF DRAWINGS

FIG. 1 is a graph showing absolute change from baseline in $GET_{1/2}$ following single oral administration of Compound A to healthy male human subjects.

DESCRIPTION OF EMBODIMENTS

Compound A, 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid is disclosed in WO2006/090224.

Compound A of this invention includes solvates, hydrates, complexes, polymorphs, prodrugs, isomers, and isotopically-labelled compounds.

Also, the present invention provides a pharmaceutical composition for the treatment of gastrointestinal diseases in an animal subject including a mammalian subject, which comprises administering to the subject above a therapeutically effective amount of Compound A or a pharmaceutically acceptable salt thereof.

Further, the present invention also provides a pharmaceutical composition for the treatment of gastrointestinal diseases, which comprises a therapeutically effective amount of Compound A or its pharmaceutically acceptable salt together with a pharmaceutically acceptable carrier.

Also, the present invention provides a method for the treatment of gastrointestinal diseases in an animal subject including a mammalian subject, which comprises administering to the subject above in need a therapeutically effective amount of Compound A or a pharmaceutically acceptable salt thereof. Further, the present invention provides a method for the treatment of gastrointestinal diseases in an animal subject including a mammalian subject, which comprises administering to the animal subject including a mammalian subject Compound A or a pharmaceutically acceptable salt thereof. Furthermore, the present invention provides use of Compound A or a pharmaceutically acceptable salt thereof in the manufacture of a medicament for the treatment of gastrointestinal diseases in an animal subject including a mammalian subject.

The term "animal subject", as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

The term "treating", as used herein, refers to reversing, alleviating, inhibiting, or preventing the onset or the progression of the disorder or condition to which such term applies, or one or more symptoms of such disorder or condition. The term "treatment" as used herein refers to the act of treating, as "treating" is defined immediately above.

The present invention also includes isotopically-labelled compounds of Compound A, but for the fact that one or more atoms can be replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}$, and $^{36}Cl$, respectively. Compound A of the present invention, prodrugs thereof, pharmaceutically acceptable esters thereof and pharmaceutically acceptable salts of the said compound, of said esters or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated hydrogen, i.e., $^3H$, and carbon-14, i.e., $^{14}C$, isotopes are particularly preferred for their ease of presentation and detectability. Further, substitution with heavier isotopes such as deuterium, i.e., $^2H$, can afford therapeutic advantage resulting from greater metabolic stability, for example increased in vivo half-life or reduced dosage requirement and, hence, may be preferred in some circumstances. Isotopically labelled compounds of Compound A of this invention and prodrugs thereof can generally be prepared by carrying out the procedure disclosed in the patent publication (WO2006/090224), and by substituting a readily available isotopically labelled reagent for a non-isotopically labelled reagent.

The present invention includes salt forms of Compound A as obtained.

As Compound A of this invention is a basic compound, they are capable of forming a wide variety of different salts with various inorganic and organic acids.

The acids which are used to prepare the pharmaceutically acceptable acid addition salts of the basic compounds of this invention of Compound A are those which form non-toxic acid addition salts. The acid addition salts can be prepared by conventional procedures.

For a review of suitable salts, see Berge S. M. et al., J. Pharm. Sci., 66, 1-19, 1977.

Also included within the scope of this invention are bioprecursors (also called "prodrugs") of Compound A. A bioprecursor of Compound A is a chemical derivative thereof which is readily converted back into the parent compound of Compound A in biological systems. In particular, a bioprecursor of Compound A is converted back to the parent Compound A after the bioprecursor has been administered to, and absorbed by, an animal subject including a mammalian subject, e.g., a human subject. Further information on the use of prodrugs may be found in Prodrugs as Novel Delivery Systems, Vol. 14, ACS Symposium Series, 1975 (T Higuchi and W Stella) and Bioreversible Carriers in Drug Design, Pergamon Press, 1987 (ed. E B Roche, American Pharmaceutical Association).

When Compound A of this invention forms solvates such as hydrates, such solvates are included within the scope of this invention.

For treating or preventing gastrointestinal diseases including gastroparesis, a suitable dosage level of Compound A of this invention to an adult human (60 kg/weight) is about 0.0001 to 1000 mg per day, preferably about 0.001 to 100 mg per day, and more preferably about 0.005 to 50 mg per day. The compound may be administered on a regimen of 1 to 4 times per day. In some cases, however, a dosage outside these limits may be used.

Compound A of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., it may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matters or dyes, and, if so desired, emulsifying and/or suspending agents as well, together with such diluents as water, ethanol, propylene glycol, glycerin and various like combinations thereof.

For parenteral administration, solutions of Compound A of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art. Additionally, it is also possible to administer Compound A of the present invention topically when treating inflammatory conditions of the skin and this may preferably be done by way of creams, jellies, gels, pastes, ointments and the like, in accordance with standard pharmaceutical practice.

Also, the present invention provides a pharmaceutical composition for the treatment of gastrointestinal diseases in an animal subject including a mammalian subject, which comprises administering to the subject above a therapeutically effective amount of Compound A or pharmaceutically acceptable salts thereof.

Further, the present invention also provides a pharmaceutical composition for the treatment of gastrointestinal diseases, which comprises a therapeutically effective amount of Compound A or its pharmaceutically acceptable salt together with a pharmaceutically acceptable carrier.

The invention also provides a method of treating gastrointestinal (GI) diseases, or preventing or delaying the onset or the progression of gastrointestinal diseases, by administering a therapeutically effective amount of Compound A of this invention or a pharmaceutically acceptable salt thereof to a patient or an animal subject including a mammalian subject in need thereof, wherein gastrointestinal diseases are associated with the reduced GI motility.

In a further aspect, the invention provides the use of Compound A or a pharmaceutically acceptable salt thereof in the manufacture of a medicament for treating gastrointestinal diseases, or preventing or delaying the onset or the progression of gastrointestinal diseases.

One embodiment of the present invention is a combination of Compound A and a drug for gastrointestinal diseases. A "combination" according to the invention may be present as a "fix combination" or as a "kit of parts combination". A "fix combination" is defined as a combination wherein the (i) at least one drug for gastrointestinal diseases; and (ii) Compound A are present in one unit. A "kit of parts combination" is defined as a combination wherein the (i) at least one drug for gastrointestinal disease; and (ii) Compound A are present in more than one unit. The components of the "kit of parts combination" may be administered simultaneously, sequentially or separately. The molar ratio of the drug for gastrointestinal diseases to Compound A is used according to the invention in within the range of from 1:100 to 100:1, such as from 1:50 to 50:1 or from 1:20 to 20:1 or from 1:10 to 10:1. The two drugs may be administered separately in the same ratio. Examples of acid secretion inhibiting agents are other 5-HT4 agonists, proton pump inhibitors, H2 receptor antagonists, and drugs for IBS (Irritable Bowel Syndrome) or constipations. These examples are H2 blocking agents such as cimetidine, ranitidine; as well as proton pump inhibitors such as pyridinylmethylsulfinyl benzimidazoles such as omeprazole, esomeprazole, lansoprazole, pantoprazole, rabeprazole or related substances such as leminoprazole.

Another embodiment of the present invention is a combination of Compound A and a drug for gastrointestinal diseases. The definition of "combination" is same as described above. Such drugs include (1) Neurokinin) receptor antagonists, such as aprepitant and maropitant, (2) 5-HT3 receptor antagonist such as palonosetron, granisetron, indisetron, ondansetron, and ramosetron, (3) steroids such as dexamethasone, prednisolone, and betamethasone, (4) dopamine receptor antagonist such as domperidone and metoclopramide, (5) antipsychotic drug such as chlorpromazine, haloperidol, prochlorperazine, (6) anti-anxiety drug such as diazepam, alprazolam, nitrazepam and lorazepam, flunitrazepam, lormetazepam, clonazepam, midazolam, oxazepam, and clobazam, (7) antidepressant drugs, such as olanzapine, and clozapine, (8) antihistamines such as diphenhydramine and (9) antidiabetic drugs, such as sulfonylurea including tolbutamide, gliclazide, chlorpropamide, glibenclamide, glybuzole, glymidine, nateglinide, and mitiglinide; biguanide including metformin and buformin; aldose reductase inhibitor including epalrestat; alpha-glucosidase inhibitor including acarbose, miglitol, voglibose; insulin-sensitizing agent including pioglitazone; DPP-4 inhibitor including sitagliptin, vildagliptin, alogliptin and (10) antiparkinson drugs, such as dopamine precursors including levodopa, dopamine agonists including bromocriptine and talipexole, dopamine release promotors including amantadine, noradrenaline precursors including droxidopa, MAO-B inhibitors including selegiline, COMT inhibitors including entacapone, and anti-cholinergics including trihexyphenidyl and biperiden.

Symptoms of gastroparesis include nausea, vomiting, postprandial bloating, epigastric pain, anorexia, and early satiety. In more severe cases, patients may vomit undigested food eaten a few hours before and may have a positive percussion splash sign along with signs of weight loss, dehydration, and malnutrition. Systemic causes of gastroparesis are evaluated by testing the patient for diabetes mellitus, hypothyroidism, cortisol deficiency, hypercalcemia, and pregnancy. Barium swallow, endoscopy, and upper GI series can rule out peptic ulcer disease and gastric outlet obstruction. Poor emptying of barium from the stomach may indicate slow gastric emptying. However, gastric scintigraphy is the gold standard for the proper diagnosis of gastroparesis. In this test, the patient is asked to eat a meal labeled with 99-M Technetium ($T_c$) sulfur colloid or other radioactive ligand. The radioactivity is then measured in the stomach region using a gamma camera. The meal should be solid because emptying a liquid meal does not represent the actual gastric emptying. The results of the test can be reported as the time of emptying 50% of the meal or the percentage of emptying at specific intervals. [Thomforde, G. M. et al., Evaluation of an inexpensive Screening scintigraphic test of gastric emptying, J. Nucl. Med. 36, 93-96 (1995)]. A breath test using $^{13}C$-labeled food can also be used to measure gastric emptying. $^{13}C$ is absorbed when it reaches the small bowel, and its measurements in the breath can indicate the gastric emptying. [Ghoos, Y. F., et al., Measurement of gastric emptying rate of solids by means of a carbon-labeled octanoic acid breath test, Gastroenterology, 104, 1640-1647 (1993)]. Electrogastrography (EGG) which measures electrical activity with cutaneous electrodes similar to those used in electrocardiograms can also be used to diagnose gastroparesis. [Stern, R. N. et al. Electrogastrography: Current issues in validation and methodology, Psychophysiology, 24, 55-64 (1987)].

EXAMPLES

The invention is further illustrated by reference to the following examples. It will be apparent to those skilled in the art that many modifications, both of materials and methods, may be practiced without departing from the purpose and scope of the invention.

Example 1

Measurement of Gastric Emptying Rates in Conscious Dogs

Animals

Four male beagle dogs weighing 9.9-13.1 kg are used. All dogs are purchased from Kitayama Labes Co., Ltd. (Oriental Yeast Co., Ltd.). The animals are acclimatized to the laboratory conditions during experiments.

Test Meal Preparation

The test meal is prepared according to the method of Sako F et al. Eur. J. Pharmacol. 395, 165-172, 2000 with a minor modification. Namely, caloric semi-solid meals (OKUNOS-A; 14.2 g carbohydrates, 5.1 g protein, 2.7 g fat, 104 kcal per 100 mL; Horika-foods, Niigata, Japan) thoroughly mixed with 1 mg/mL of acetaminophen (Wako Pure Chemical Industries, Ltd., Osaka, Japan).

Experimental Procedures (1) Preparation of Clonidine-Induced Gastroparesis Model The gastric emptying is assessed by the acetaminophen method (Heading R C et al. Br. J. Pharmacol. 47, 415-421, 1973). Dogs are fasted overnight, and then they are fed the test meal (10 mL/kg), which is ingested within 3 minutes.

Blood samples are obtained at 0, 15, 30, 45, 60, 75, and 90 minutes after test meal administration. To provide a model of gastroparesis, 0.01 mg/kg of clonidine (alpha2 adrenergic agonist, Wako Pure Chemical Industries, Ltd., Osaka, Japan) is injected subcutaneously 30 minutes before test meal administration. Compound A, cisapride, or vehicle is administered orally immediately before the administration of clonidine. Plasma is separated from the blood by centrifugation at 3,000 g for 5 min at 4° C. (himac CF15D, Hitachi Koki Co., Ltd., Tokyo, Japan). The plasma acetaminophen concentration is measured by LC-mass spectrometry.

(2) Analysis Method for the Determination of Acetaminophen Concentration in Dog Plasma (2-1) Analytical Instrumentations API4000 Triple Quadrupole Mass Spectrometer (AB SCIEX, Foster City, Calif., USA) Agilent 1100 HPLC system (Agilent Technologies, Santa Clara, Calif., USA) Shimadzu SIL-HTc autosampler (Shimadzu Corporation, Kyoto, Japan)

(2-2) Extraction of Acetaminophen from Dog Plasma

Aliquots of dog plasma (50 microL) and 50 microL of internal standard (IS)* solution are mixed and vortexed well, and then they are diluted to a final volume of 750 microL with 50 mM ammonium acetate. As IS, $[D_4]$4-acetamidophenol is used. Following conditioning of the solid phase extraction (SPE) 96 well plate (OASIS HLB, 10 mg/well, 30 microm, Waters Corporation, Milford, Mass., USA) with 700 microL methanol and 700 microL water in sequence, 750 microL of the plasma samples are transferred to the SPE plate for extraction. The SPE plate is then washed with 700 microL of 5% methanol. Samples are eluted twice off the SPE plate into a clean 96 deep well plate by addition of 250 microL of methanol. The eluent is then evaporated to dryness under 40° C. gentle stream of nitrogen, and reconstituted in 100 microL of acetonitrile/10 mM ammonium acetate (1/9, v/v). The samples are injected into HPLC column, and then the effluent from HPLC column is directly introduced into the turboionspray ion source, which is operated at the following conditions:

* 300 ng/mL $[D_4]$4-acetamidophenol: 10% methanol solution.

(2-3) Analytical Conditions

HPLC Condition

Column: Atlantis dC18 3 microm, 4.6 mm I.D.×50 mm (Waters Corporation, Milford, Mass., USA)

Mobile phase: Acetonitrile/10 mM ammonium acetate pH 3.5 (2/3)

Flow rate: 0.8 mL/min

Acquisition time: Isocratic: 2.5 min

Column temperature: 40° C.

Autosampler temperature: 15° C.

Autosampler wash solution: Methanol

Injection volume: 10 microL (2-4) MS Condition

Ion source: Electrospray (TurbolonSpray), positive

Scan type: Multiple Reaction Monitoring (MRM)

Monitoring Mass:

TABLE 1

| Compound | Q1(amu[1]) | Q3(amu) | DP[2](V) | CE[3](V) | CXP[4](V) |
|---|---|---|---|---|---|
| Acetaminophen | 152.1 | 110.0 | 51 | 23 | 8 |
| $[D_4]$4-acetamidophenol | 156.1 | 114.1 | 56 | 23 | 8 |

[1]amu stands for atmic mass unit.
[2]DP stands for declustering potential.
[3]CE stnds for collision energy.
[4]CXP stands for collision cell exit potential.

Collision gas (CAD): 5

Curtain gas (CUR): 10

Ion source gas 1 (Gas1): 20

Ion source gas 2 (Gas2): 70

Ion Spray voltage (IS): 5000 V

Temperature (TEM): 600° C.

Results

Gastric emptying expressed as an elevated plasma acetaminophen (APAP), proceeded rapidly after the test meal is ingested. Subcutaneous administration of clonidine at a 0.01 mg/kg dose significantly decreased plasma APAP concentration at 60 min after meal administration in dogs. Therefore, we used this clonidine dose as a gastroparesis model.

Oral administration of Compound A (0.3 microg/kg) significantly restored delayed gastric emptying induced by clonidine (0.01 mg/kg) to the normal levels. Cisapride (1, 3 mg/kg) also reversed delayed gastric emptying.

Discussion

Compound A accelerated gastric emptying under the condition of clonidine-induced gastroparesis. The acceleratory effect of Compound A (0.3 microg/kg, p.o.) is equivalent to that of cisapride (1 mg/kg, p.o.). Compound A is approximately 3,000 times more potent than cisapride in enhancing gastric emptying in this model.

Example 2

Measurement of Gastric Emptying Rates in Human Study Population

Healthy male subjects, who aged between 18 and 55 years old and have a normal gastric emptying (GE) rate, are screened and enrolled into the study.

Treatment Administration

Subjects are given single oral doses of Compound A at 0.6 and 3 microg. Subjects swallowed dosing solution (20 mL) of appropriate Compound A concentrations. The dosing bottle is rinsed with 20 mL of water, and this rinse is swallowed by the subjects. The subjects then swallowed 200 mL of room temperature water, resulting in a total fluid intake at dosing of 240 mL.

Pharmacodynamic Assessments

GE is monitored with $^{13}$C-breath test using the BreathiD system (Exalenz Bioscience Inc., Modin, Israel), which enables to continuously analyze the subject's breath for exhaled $CO_2$ via a nasal cannula using molecular correlation spectrometry at the bedside. The system calculates the ratio of $^{13}CO_2:^{12}CO_2$ in exhaled air and expresses the ratios as delta over baseline. Breath ID measurements are conducted at 1.5 hour postdose. GE rate of solids is evaluated over the 4 hours period following ingestion of a standardized solid test meal, which are comprised of 2 slices of bread, 1 egg and 150 mL water including an egg yolk that have been mixed with 100 mg $^{13}$C-octanoic acid (total calorific intake of 200-300 kcal). The test meal is consumed within 10 minutes, just prior to the BreathID measurements. The subjects have a baseline BreathID measurement for ca. 3 minutes before test meal ingestion following measuring their body weight. The parameters for GE of gastric half emptying time ($GET_{1/2}$), lag phase ($T_{lag}$), gastric emptying coefficient (GEC) and gastric emptying area under the effect curve (AUEC) are automatically calculated.

Results of changes from baseline in $GET_{1/2}$ are summarized in FIG. 1.

Absolute change from baseline in $GET_{1/2}$ following single oral administration of Compound A to healthy male human subjects is clearly observed. No Severe Adverse Events (SAEs) and undesirable adverse events including cardiovascular events such as QT/QTc prolongation, which has been main reasons of cisapride withdrawal, are observed even at supratherapeutic doses of Compound A in human healthy subjects.

Example 3

Measurement of Gastric Emptying Rates in Patients with Gastroparesis Clinical studies in patients with gastroparesis are conducted. Effect of Compound A on gastric emptying time (GET) is confirmed with SmartPill (Registered Trademark, Given Imaging Ltd.). SmartPill is an ingestible capsule that measures pressure, pH and temperature as it travels through the gastrointestinal (GI) tract to assess GI motility. The SmartPill motility monitoring test can be performed at a clinic or physician's office to evaluate motility disorders like gastroparesis (a condition in which the contents of the stomach empty too slowly) and chronic constipation. An improved gastric emptying time and colonic transit time are observed in the clinical studies.

The invention claimed is:

1. A pharmaceutical composition which comprises a therapeutically effective amount of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof, for treatment of gastroparesis wherein said gastroparesis is caused by at least one condition selected from the group consisting of diabetes, postviral syndromes, anorexia nervosa, surgery of the stomach or vagus nerve, amyloidosis, scleroderma, abdominal migraine, Parkinson's disease, hypothyroidism, multiple sclerosis, and drugs including anticholinergics, calcium channel blockers, opioids, antidepressants, or said gastroparesis is a symptom of any of the foregoing conditions.

2. The pharmaceutical composition of claim 1, which further comprises a therapeutically effective amount of one or more additional compounds known to be useful in the treatment of gastroparesis or the symptoms thereof.

3. A method for the treatment of gastroparesis in an animal subject including a mammalian subject in need of such treatment, which comprises administering to the said subject an effective amount of 4-{[4-({[4-(2,2,2-trifluoroethoxy)-1,2-benzisoxazol-3-yl]-oxy}methyl)piperidin-1-yl]methyl}tetrahydro-2H-pyran-4-carboxylic acid or a pharmaceutically acceptable salt thereof, wherein said gastroparesis is caused by at least one condition selected from the group consisting of diabetes, postviral syndromes, anorexia nervosa, surgery of the stomach or vagus nerve, amyloidosis, scleroderma, abdominal migraine, Parkinson's disease, hypothyroidism, multiple sclerosis, and drugs including anticholinergics, calcium channel blockers, opioids, antidepressants, or said gastroparesis is a symptom of any of the foregoing conditions.

4. The method for the treatment of gastroparesis described in claim 3, wherein at least one symptom of gastroparesis is relieved.

5. The method described in claim 3, which comprises further administering a therapeutically effective amount of one or more additional compounds known to be useful in the treatment of gastroparesis.

6. The method described in claim 4, which comprises further administering a therapeutically effective amount of one or more additional compounds known to be useful in the treatment of gastroparesis.

* * * * *